United States Patent
Petersen-Braun et al.

(10) Patent No.: US 9,867,789 B2
(45) Date of Patent: Jan. 16, 2018

(54) NON-STEROIDAL ANTI-INFLAMMATORY DRUGS FOR COUGH

(75) Inventors: Marianne Petersen-Braun, Königswinter (DE); Chirin Yekrangi-Hartmann, Mettmann (DE); Uwe Gessner, Rösrath (DE); Michael Völker, Köln (DE)

(73) Assignee: BAYER CONSUMER CARE AG, Basel (CH)

( * ) Notice: Subject to any disclaimer, the term of this patent is extended or adjusted under 35 U.S.C. 154(b) by 0 days.

(21) Appl. No.: 13/535,132

(22) Filed: Jun. 27, 2012

(65) Prior Publication Data

US 2012/0277318 A1 Nov. 1, 2012

Related U.S. Application Data

(63) Continuation of application No. 12/386,531, filed as application No. PCT/EP2007/008737 on Oct. 9, 2007, now abandoned.

(30) Foreign Application Priority Data

Oct. 20, 2006 (EP) .................................. 06022042

(51) Int. Cl.
*A61K 31/192* (2006.01)
*A61K 31/00* (2006.01)

(52) U.S. Cl.
CPC ............ *A61K 31/00* (2013.01); *A61K 31/192* (2013.01)

(58) Field of Classification Search
CPC ................................. A61K 31/00; A61K 31/192
See application file for complete search history.

(56) References Cited

U.S. PATENT DOCUMENTS 5,025,019 A * 6/1991 Sunshine et al. ............. 514/277
2004/0029864 A1 * 2/2004 MacMillan ............... 514/217.05

FOREIGN PATENT DOCUMENTS

CA 2148768 A1 11/1995

OTHER PUBLICATIONS

Dales et al. (Pharmacotherapy 1992, vol. 12, pp. 331-333).*
Choudry et al.(European Respir J, 1992, vol. 5, pp. 296-300).*
Chung et al. (postgrad medical journal, 1996, vol. 72, pp. 594-598).*
English language abstract of Anania, A., et al., Farmaci antinfiammatori e reattivita bronchiale, Minerva Pneumologica, 1995, vol. 34, No. 3, pp. 113 to 117.
McEwan, J., et al., The Effect of Sulindac on the Abnormal Cough Reflex Associated with Dry Cough, J. Pharmacol. Exp. Ther., 1990, vol. 255, No. 1, pp. 161 to 164.
Tenenbaum, A., et al., Intermediate but not Low Doses of Aspirin Can Suppress Angiotensin-Converting Enzyme Inhibitor-Induced Cough, American Journal of Hypertension, Jul. 2000, vol. 13, No. 7, pp. 776 to 782.
Notice of Opposition to a European Patent. Opposition by Reckitt Benckiser (Brands) Limited to European Patent No. EP 2106258B1 / Application No. 07818811.7 Entitled "Ibuprofen Against Coughing" in the Name of Bayer Consumer Care AG.
Pujet et al "Comparative Study of Two Antitussive Drugs in the Treatment of Acute Dry Cough of Infectious Origin (Prospective, Randomized, Single Blind Study", Therapie, Doin, Paris, FR, Bd. 57, No. 5 (Sep. 1, 2002), 457-463, XP008097000.
Ulukol et al. "Assessment of the Efficacy and Safety of Paracetamol, Ibuprofen and Nimesulide in Children With Upper Respiratory Tract Infections", Eur J. Clin. Pharmacol (1999) vol. 55, 615-618.
"Cough Medicine" Wikipedia, (Sep. 25, 2014) pp. 1-6.
"Clobutinol" Wikipedia, (Sep. 26, 2014) pp. 1-4.
"Oxomemazin", "Oxomemazineiguaifenesin" Und "Guaifenesin", Wikipedia (Sep. 26, 2014) pp. 3-12.
"Tracheitis", "Akute Bronchitis" Und "Rhinopharyngitis", Wikipedia (Sep. 26, 2014) pp. 1-12.
Winther et al. "Potential Benefits of Ibuprofen in the Treatment of Viral", Inflammopharmacology, (2003) vol. 11, No. 4-6, pp. 445-452.

* cited by examiner

*Primary Examiner* — Savitha Rao
(74) *Attorney, Agent, or Firm* — McBee Moore Woodward & Vanik IP, LLC

(57) ABSTRACT

The use of a non-steroidal anti-inflammatory drug for the treatment of nonproductive cough caused by viruses or bacteria and a combination of at least one non-steroidal anti-inflammatory drug with at least one antitussive in a formulation to treat coughs.

5 Claims, No Drawings

NON-STEROIDAL ANTI-INFLAMMATORY DRUGS FOR COUGH

The present invention relates to the use of non-steroidal anti-inflammatory drugs as antitussive and to their use for the manufacture of a medicament for the treatment of nonproductive cough associated with disorders of the respiratory organs caused by viruses or bacteria, especially common colds. The invention also relates to pharmaceutical formulations for the treatment of nonproductive cough associated with viral or bacterial disease of the respiratory organs which comprise a combination of at least one non-steroidal anti-inflammatory drug with at least one antitussive.

Ibuprofen is an arylpropionic acid derivative whose pain-relieving (analgesic), fever-reducing (antipyretic) and inflammation-inhibiting (anti-inflammatory) effect has been known for a long time. It is used as active ingredient in a large number of medicaments for oral, parenteral and topical or rectal administration. Ibuprofen-containing products are employed as means for treating mild to moderately severe pain such as headache, toothache, sore throat, period pain, joint pain, backache, and in the treatment of the acute headache phase in migraine with and without aura and the treatment of tension headaches. Further areas of use of ibuprofen are the treatment of inflammatory and degenerative types of rheumatism, soft-tissue rheumatism and non-rheumatic inflammatory pain, of arthroses, inflammatory rheumatic disorders of the joints and spinal column, swelling and inflammations of the soft tissue near joints, shoulder stiffness, low back pain, lumbago, sports and accident injuries. Ibuprofen-containing products are also employed for the symptomatic treatment of febrile conditions.

Ibuprofen is an active ingredient belonging to the group of non-steroidal anti-inflammatory drugs. Non-steroidal anti-inflammatory drugs are inhibitors of cyclooxygenases and can be obtained commercially in a number of different oral and parenteral dosage forms. Creams and gels are available for topical application of nonselective cyclooxygenase inhibitors. Also available as further parenteral dosage forms are suppositories and solutions for injection. Parenteral dosage forms for selective inhibitors of cyclooxygenase 2 are unavailable, at least commercially. Dosage forms available for oral administration of non-steroidal anti-inflammatory drugs are tablets, film-coated tablets, slow-release tablets, sugar-coated tablets, capsules, slow-release capsules, granules, suspensions and effervescent tablets.

It is known that ibuprofen-containing products are used for treating the symptoms of common colds caused by viruses, such as fever, headache, sore throat and aching limbs. On the other hand, the active ingredients used for treating the cough which is likewise associated with common colds are different and are from the group of expectorants or the group of antitussives such as codeine, dihydrocodeine, hydrocodone, clobutinol, pentoxyverine, pipazetate, noscapine, dextromethorphan or plant constituents.

Cough is normally regarded as a symptom of a disorder but, apart from idiopathic cough, not as a separate disease. Cough (tussis) refers to the voluntary or involuntary, induced via the cough reflex on the basis of an urge to cough, explosive expulsion of air intended to free the airways of foreign bodies or mucus which might block or constrict them. Cough is thus normally one of the body's protective and cleansing mechanisms.

Cough is differentiated into various types. A distinction is made essentially between dry cough (nonproductive) and the productive cough characterized by copious formation of mucus. A further differentiation is made between acute and chronic cough according to the duration.

Dry cough (hacking cough) is distinguished by spasmodic, severe coughing attacks in which no mucus is expelled. It occurs suddenly and is usually only of short duration, but may also persist for several weeks. In cases of hacking cough, the cough itself does not lead to a reduction in the urge to cough.

Productive cough occurs when the bronchial secretion (mucus) in the airways can no longer be removed by the cleansing power of the cilia. The intention then is to detach and transport away the secretion by the coughing. The urge to cough is usually very strong in cases of productive cough but declines after expulsion of the bronchial secretion.

In "smoker's cough", which is also referred to as chronic productive cough and may also occur in nonsmokers, owing to the permanent damage to the cilia resulting from long-term irritation of the bronchi, there is an enlargement of the glands in the bronchial mucosa and an increased mucus production. Instead of the natural self-cleansing mechanism there is a strong urge to cough in order to transport away the mucus. This cough occurs more commonly in the early hours of the morning and is a sign of chronic bronchitis.

Cold cough is a common symptom of influenzal infections, i.e. of infections almost always caused by viruses of the respiratory organs. Shortly after the viruses have become established in the bronchi, a dry hacking cough develops owing to the mucosal irritation and develops into an expectorant productive cough. If the mucous expectoration is yellowish, greenish or brownish in colour, this is a sign of a bacterial infection. When the cold is declining, the symptoms diminish and the cough is converted back into a dry cough and/or disappears.

Common colds and the so-called "influenzal infections" which are normally attributable to an infection with viruses are regarded as the commonest cause of cough.

A particular example to be mentioned of nonproductive cough caused by bacteria is whooping cough. Whooping cough is a severe infectious disease caused by the bacterium *Bordetella pertussis*.

Whopping cough can be divided into three stages. It starts about five to fourteen days after the infection with the so-called "catarrhal stage" which lasts one to two weeks. In this stage, the infected person suffers from influenza-like symptoms such as sneezing, running nose, sore throat, slight cough and moderate fever. This is followed by the stage characteristic of this disease (paroxysmal stage) which lasts about four to six weeks. The cough becomes worse and occurs spasmodically in the form of several successive severe attacks of coughing, followed by a sudden inhalation with a loud gasp. During these attacks of coughing, mucus may be brought up and then vomited. The attacks of coughing occur frequently at night and may be induced by external causes such as, for example, physical exertion or psychological factors. Between the attacks of coughing, those affected are usually not incommoded by the disease and do not suffer from fever. In the late stage of the disease, the so-called "convalescent stage", there is a gradual decline in the episodes of coughing. This phase of nonproductive cough usually lasts, without antibiotic treatment, six to ten weeks after the febrile phase of the disease has resolved.

However, possible causes of cough are not only disorders of the respiratory organs but may also be disorders of the heart or stomach. In addition, however, intake of medicaments or, in rare cases, a psychological disorder may underlie the cough.

Cough is treated by administration either of medicaments which promote the expectoration of bronchial secretion (expectorants) or medicaments suppressing the urge to cough (antitussives).

The expectorants are differentiated according to the mechanism of action into secretolytics or mucolytics which achieve liquefaction of the bronchial secretion, and secretomotor agents which induce an increased transport away of the bronchial mucus.

Examples of secretolytics are acetylcysteine, bromhexine and its metabolite ambroxol, ammonium chloride and guaifenesin, but also plant products such as fennel oil and anise oil.

Most antitussives are opiate derivatives and thus prescription only medicaments. Examples in use are codeine, dihydrocodeine, dextromethorphan and hydrocodone, which has particularly strong activity and is covered by the narcotics legislation. These substances act via the central nervous system and have, besides a depressant effect on the cough centre in the brainstem, also a calming (sedative) effect.

Substances which can be employed as alternatives are those having no addictive potential and no sedative effect either. This group of active ingredients includes clobutinol and the somewhat less effective pentoxyverine.

The urge to cough can also be alleviated alternatively by taking certain plant products.

Medicaments which suppress the urge to cough should be given only for nonproductive cough. Combination with mucolytic agents (expectorants) is counterproductive because it is then not possible to cough up the mucus produced.

The use of ibuprofen in combination with an antitussive for the treatment of cough associated with common colds is not only usual and described in many publications but also the subject of numerous patent publications. For example, EP 0 274 845 A1 discloses a stable, solid pharmaceutical preparation which comprises ibuprofen or a pharmaceutically acceptable salt of ibuprofen in combination with codeine or a pharmaceutically acceptable salt of codeine and an insoluble salt of carboxymethylcellulose in an amount preventing discoloration of the preparation.

However, in the known active ingredient combinations with an antitussive, ibuprofen is employed exclusively as analgesic or as antipyretic together with the antitussive.

On the other hand, there are only a few reports in the literature on the treatment of cough with single-drug products having analgesic activity. Thus, Ulukol et al. (Eur. J. Clin. Pharmacol. 1999; 55: 615-618) described the reduction in the symptoms of cough after treatment with ibuprofen in a dosage of 10 mg/kg in a study on 30 children suffering from a feverish infection of the upper respiratory organs.

During this study, children with a feverish cold of the upper respiratory organs were treated for 5 days either with paracetamol (10 mg/kg 3× a day), with ibuprofen (10 mg/kg 3× a day) or nimesulide (2.5 mg/kg 2× a day). It emerged from this that the fever-reducing effect of nimesulide was better and faster than that of paracetamol or ibuprofen. An alleviation of the symptoms of cough was greater in the children treated with paracetamol than in the children who received one of the two other active ingredients.

However, this study was not a double-blind study, nor did it include a placebo group as control. It is therefore not to be regarded as a controlled study. Since common colds moreover are self-limiting disorders, an effect suppressing the urge to cough and attributable to ibuprofen cannot be inferred from this study.

In an observation of the case of a 57-year-old woman with idiopathic chronic cough, i.e. cough of unknown cause, a reduction in the number of coughing episodes compared with placebo was found with ibuprofen therapy in a dosage of 600 mg three times a day for 6 days (Dales et al., Pharmacotherapy 1992; 12: 331-333). However, it is noteworthy that the amount of ibuprofen administered, a daily dose of 1800 mg, was substantially higher than the dose of from 400 to a maximum of 1200 mg/day which is intended for the OTC sector (OTC=over-the-counter).

However, administration of ibuprofen or another non-steroidal anti-inflammatory drug as single-drug product for the treatment of cough as symptom of diseases caused by viruses or bacteria in the respiratory organs, especially of coryzal conditions, is not known.

The present invention relates to the use of a non-steroidal anti-inflammatory drug for the treatment of nonproductive cough caused by viruses or bacteria, and for the manufacture of a medicament for the treatment of nonproductive cough caused by viruses or bacteria, especially in the phase of the disorder when the hacking cough is diminishing.

The non-steroidal anti-inflammatory drug is preferably an inhibitor of cyclooxygenase, both a selective and a nonselective inhibitor of cyclooxygenase being possible.

In a preferred embodiment of the invention, the non-steroidal anti-inflammatory drug is selected from the group consisting of non-selective cyclooxygenase inhibitors. Examples of non-selective cyclooxygenase inhibitors which are suitable for the use according to the invention and may be selected are ibuprofen, acetylsalicylic acid, methyl salicylate, diflunisal, benorylate, naproxen, diclofenac, sulindac, carprofen, fenoprofen, flurbiprofen, ketoprofen, ketorolac, loxoprofen, indomethacin, tiaprofenic acid, mefenamic acid, meclofenamic acid, phenylbutazone, oxyphenbutazone, meloxicam, lornoxicam, piroxicam and nimesulide.

In another preferred embodiment, the non-steroidal anti-inflammatory drug is selected from the group of selective inhibitors of cyclooxygenase 2. Examples to be mentioned of selective cyclooxygenase 2 inhibitors which are suitable for the use according to the invention and may be selected are celecoxib, lumiracoxib, etoricoxib, parecoxib, valdecoxib and rofecoxib.

The substances cited by way of example do not represent a complete and definitive list of selective and nonselective inhibitors of cyclooxygenase suitable for the use according to the invention, and they are mentioned merely for illustration thereof.

It is, of course, also possible to use other selective and/or nonselective inhibitors of cyclooxygenase for the purpose of the invention. In addition, the selective and nonselective cyclooxygenase inhibitors may in preferred embodiments of the present invention also be used in the form of their pharmacologically acceptable salts.

In a preferred embodiment of the invention, ibuprofen is used as active pharmaceutical ingredient for the manufacture of the medicament for the treatment of cough caused by viruses or bacteria. It is possible in this connection to use ibuprofen both in the form of a racemic mixture of its two enantiomers (R-ibuprofen and S-ibuprofen) and in the form of one of its two enantiomers, the pharmacologically active S-ibuprofen, or R-ibuprofen which is converted in vivo into the pharmacologically active S-ibuprofen, as well as a salt or hydrate thereof.

In a preferred embodiment, the medicament for the treatment of nonproductive cough caused by viruses or bacteria is a single-drug product, i.e. a medicament which comprises one non-steroidal anti-inflammatory drug, preferably ibuprofen or a pharmaceutically acceptable salt or derivative of ibuprofen, as sole active pharmaceutical ingredient.

The particular advantage of this single-drug product is that the non-steroidal anti-inflammatory drug alleviates, in a common cold caused by viruses, not only the symptom of cough but also the other usual symptoms of fever and pain (headaches, aching limbs and muscles) without intake of further medicaments being necessary.

TABLE 1

Amounts of active ingredient present as unit dose in formulations of various non-steroidal anti-inflammatory drugs

| Active ingredient | Amount of active ingredient [mg] |
|---|---|
| Ibuprofen | 200, 400, 600, 800 |
| Ketoprofen | 50, 100, 200 |
| Naproxen | 220, 250, 500, 660, 750 |
| Diclofenac | 12.5, 25, 50, 100 |
| Celecoxib | 100, 200 |
| Rofecoxib | 12.5, 25 |
| Valdecoxib | 10, 20, 40 |

The medicaments obtainable according to the use according to the invention may comprise the non-steroidal anti-inflammatory drug in usual dosages which depend on the active pharmaceutical ingredient used. Examples of usual amounts of active ingredient present as unit doses in formulations of non-steroidal anti-inflammatory drugs are listed in Table 1. In particular when ibuprofen or one of its pharmaceutically acceptable salts, hydrates or derivatives is used, the medicament may comprise a dose of from 50 to 3000 mg, preferably from 100 to 800 mg and particularly preferably from 200 to 400 mg ibuprofen-equivalent amount of active ingredient.

In another preferred embodiment of the invention, the non-steroidal anti-inflammatory drug is used in combination with an antitussive to manufacture a medicament for the treatment of nonproductive cough caused by viruses or bacteria. In this embodiment, the medicament obtainable according to the invention represents a combination of at least one non-steroidal anti-inflammatory drug with at least one antitussive. The advantage of a medicament according to this embodiment is that the suppressant effect of the antitussive on the urge to cough can be enhanced by the non-steroidal anti-inflammatory drug.

When a non-steroidal anti-inflammatory drug is combined with an antitussive there is observed to be a synergistic effect making it possible to reduce the dose of antitussive to be administered compared with the dose of antitussive to be administered as single-drug product. It is possible in this way to reduce possible side effects due to antitussives, to improve the utilizability during the day even of antitussives having a sedative effect and/or to prolong the dosage intervals.

"Combination" means in the context of the invention not only dosage forms which comprise all the components (so-called fixed combinations), and combination packs which comprise the components separate from one another, but also components which can be administered simultaneously or successively as long as they are employed for the treatment of the same disease/symptom.

The synergistic effect of the combination of the invention is preferably observed when the non-steroidal anti-inflammatory drug and the antitussive are present in a ratio of from 2:1 to 100:1, preferably 2.5:1 to 20:1, particularly preferably 5:1 to 10:1. "Ratio" means in the context of the invention the ratio by weight of the individual components of the combination.

The recommended daily dose for antitussives (single-drug product) is 30 to 180 mg for codeine, 30 to 90 mg for dextromethorphan, 30 to 90 mg for dihydrocodeine, up to 150 mg for noscapine, up to 200 mg for pentoxyverine and 120 to 240 mg for clobutinol.

The daily dose of antitussive to be administered can be reduced by the combination of the invention with a non-steroidal anti-inflammatory drug by up to 30%, preferably by up to 50% and particularly preferably by up to 75%.

It may be necessary where appropriate to deviate from the amounts mentioned, specifically as a function of the body weight and nature of the administration route, of the individual response to the medicament, of the type of formulation thereof and the time or interval over which administration takes place. Thus, it may be sufficient in some cases to make do with less than the aforementioned minimum amount, whereas in other cases the upper limit mentioned must be exceeded. It may in the event of administration of larger amounts be advisable to divide these into a plurality of individual doses over the day.

The medicaments and pharmaceutical formulations of the invention include dosage forms which can be administered parenterally or orally, with preference for dosage forms for oral administration.

The medicaments and pharmaceutical formulations of the invention may be solid or liquid dosage forms. Examples of solid dosage forms are tablets, orally disintegrating tablets, effervescent tablets, sugar-coated tablets, capsules, soft gelatin capsules, powders, granules, pellets, suppositories, and platelets and wafers. Examples of liquid dosage forms are elixirs, syrups, gels, preferably low-viscosity gels, suspensions and solutions.

The active ingredients of the medicaments and pharmaceutical formulations of the invention are particularly suitable for formulation in a fixed combination in the form of a solid oral dosage form. It is known that the reliability of intake (compliance) by patients is crucially dependent on the factors of the number of dosage forms per time of intake, and the size and weight of the (solid oral) pharmaceutical. The aim should therefore be to have as small a number as possible of different medicaments to be taken separately (advantage of a fixed combination) and to keep the size and weight of a solid oral dosage form as small as possible without impairing the therapeutic potency. This makes intake as convenient as possible for the patient. Fixed combinations in the form of solid oral pharmaceutical formulations with minimum size and minimum weight achieve maximum patient compliance and a crucial improvement in the safety and reliability of the therapy.

Release of active ingredients from the medicament can be controlled by modifying the composition of the medicaments or pharmaceutical formulations. For example, it is possible by delayed release of the or of one of the active ingredients in a fixed combination for the onset of action thereof to be time-decoupled even on use of fixed combinations.

The manufacture of the medicaments and pharmaceutical formulations of the invention for the treatment of nonproductive cough can take place by taking account of the non-steroidal anti-inflammatory drugs to be used according to the invention by use of the processes known for the respective dosage form and with use of pharmaceutical excipients as are familiar to the skilled person.

The solid dosage forms are manufactured by the generally known standard processes. Further ingredients are those which are pharmacologically acceptable and physiologically harmless, for example: as fillers cellulose derivatives (e.g. microcrystalline cellulose), sugar (e.g. lactose), sugar alcohols (e.g. sorbitol, mannitol), inorganic fillers (e.g. calcium phosphates), binders (e.g. polyvinylpyrrolidone, gelatin, starch derivatives and cellulose derivatives), and all further excipients required to manufacture pharmaceutical formulations with the desired properties, e.g. lubricants (magnesium stearate), disintegrants (e.g. crosslinked polyvinylpyrrolidone, sodium carboxymethylcellulose), wetting agents (e.g. sodium lauryl sulphate), release-slowing agents (e.g. cellulose derivatives, poly(meth)acrylic acid derivatives), stabilizers, flavourings and/or coloured pigments.

Liquid dosage forms are likewise manufactured by standard methods using pharmaceutically acceptable excipients and comprise the active ingredients either dissolved or suspended. Typical volumes administered of these pharmaceutical preparations are between 1 and 10 ml. Examples of excipients in these liquid formulations are: solvents (e.g. water, alcohol, natural or synthetic oils such as medium chain triglycerides), solubilizers (e.g. glycerol, glycol derivatives), wetting agents (e.g. polysorbate, sodium lauryl sulphate), and further excipients required to manufacture pharmaceutical formulations with the desired properties, e.g. viscosity-increasing agents, pH correctives, sweeteners and flavourings, antioxidants, stabilizers and/or preservatives.

The main ingredient of the shells of capsule formulations are for example gelatin or hydroxypropylmethylcellulose.

The present invention relates not only to the use of a non-steroidal anti-inflammatory drug for the treatment of nonproductive cough and for the manufacture of a medicament for the treatment of nonproductive cough, but also to pharmaceutical formulations for the treatment of nonproductive cough which comprise the combination of at least one antitussive with at least one non-steroidal anti-inflammatory drug, but also to the use of this combination for the treatment of nonproductive cough as symptom of a disease caused by viruses or bacteria. For this purpose, the antitussive and/or the non-steroidal anti-inflammatory drug are preferably selected from the groups of active ingredients mentioned previously.

The medicaments of the invention may comprise a combination of at least one non-steroidal anti-inflammatory drug with at least one antitussive in a joint dosage form, or be in the form of a "kit" which comprises in separate containers in a single pack in one container an effective amount of at least one non-steroidal anti-inflammatory drug and in another container an effective amount of at least one antitussive. The present invention thus also relates to pack units or kits which one or more units of compositions which comprise at least one non-steroidal anti-inflammatory drug, preferably ibuprofen or one of its pharmaceutically acceptable salts, hydrates or derivatives, and/or at least one antitussive and which represent a large number of single doses which are intended to be administered for the treatment of nonproductive cough as symptom of an infection caused by viruses or bacteria.

EXAMPLE

The efficacy of ibuprofen in the symptomatic treatment of nonproductive cough was determined in 3 volunteer patients in the final phase of a viral infection. For this purpose, the patients received oral administration of 400 or 800 mg of ibuprofen (the daily dose was between 400 and 1200 mg). No other medicaments were taken by the patients during the viral infection.

It was observed after administration of ibuprofen that the number of attacks of coughing was reduced by more than 50% relative to the number of attacks of coughing before administration of ibuprofen. The patients agreed in saying that the intensity of the urge to cough and the severity of the attacks of coughing were also reduced. In connection therewith it was also possible to improve the patients' rest at night without administration of an additional cough suppressant being necessary.

The effects of ibuprofen declined after 6 to 8 hours and the cough reappeared in the former severity. Subsequent renewed administrations of ibuprofen again led to the described improvement in the symptoms of cough.

What is claimed is:

1. A method for the treatment of nonproductive cough as a symptom of an infection of the respiratory organs caused by a virus or bacteria, comprising the step of administering a composition for oral administration comprising an effective amount of ibuprofen or one of its pharmaceutically active salts or hydrates to a patient in need of treatment for nonproductive cough as a symptom of an infection of the respiratory organs caused by a virus or bacteria, wherein the composition for oral administration does not comprise an expectorant or antitussive, wherein the composition for oral administration is a single-drug product comprising the ibuprofen as the sole active pharmaceutical ingredient.

2. The method of claim 1, wherein the ibuprofen is in the form of a racemic mixture of R-ibuprofen and S-ibuprofen.

3. The method of claim 1, wherein the ibuprofen is in the form of S-ibuprofen.

4. The method of claim 1, wherein the ibuprofen is in the form of R-ibuprofen.

5. The method of claim 1, wherein the ibuprofen is administered in a dose from 400 to a maximum of 1200 mg/day.

* * * * *